(12) United States Patent
Lindström

(10) Patent No.: US 11,068,828 B2
(45) Date of Patent: Jul. 20, 2021

(54) COMPLIANCE METRIC FOR THE USAGE OF HYGIENE EQUIPMENT

(71) Applicant: ESSITY HYGIENE AND HEALTH AKTIEBOLAG, Gothenburg (SE)

(72) Inventor: Håkan Lindström, Gothenburg (SE)

(73) Assignee: Essity Hygiene and Health Aktiebolag, Gothenburg (SE)

( * ) Notice: Subject to any disclaimer, the term of this patent is extended or adjusted under 35 U.S.C. 154(b) by 188 days.

(21) Appl. No.: 16/303,300

(22) PCT Filed: May 30, 2016

(86) PCT No.: PCT/EP2016/062154
§ 371 (c)(1),
(2) Date: Nov. 20, 2018

(87) PCT Pub. No.: WO2017/207018
PCT Pub. Date: Dec. 7, 2017

(65) Prior Publication Data
US 2020/0321104 A1    Oct. 8, 2020

(51) Int. Cl.
*G06Q 10/06* (2012.01)
*G16H 40/63* (2018.01)
(Continued)

(52) U.S. Cl.
CPC ....... *G06Q 10/06393* (2013.01); *G06N 20/00* (2019.01); *G16H 20/00* (2018.01);
(Continued)

(58) Field of Classification Search
CPC .. G06Q 10/06393; G16H 20/00; G16H 40/67; G16H 30/20; G16H 40/20; G16H 40/63; G06N 20/00
(Continued)

(56) References Cited

U.S. PATENT DOCUMENTS

2010/0117836 A1 *   5/2010   Seyed Momen ...... G16H 40/20
                                                                 340/573.1
2013/0290016 A1    10/2013   Alper et al.
(Continued)

FOREIGN PATENT DOCUMENTS

WO    WO-2007/026130 A1    3/2007

OTHER PUBLICATIONS

Guyon, Isabelle, et al., "An Introduction to Variable and Feature Selection," Journal of Machine Learning Research 3 (2003) 1157-1182.
(Continued)

*Primary Examiner* — Jonathan Durant
*Assistant Examiner* — Benjamin L. Hanks
(74) *Attorney, Agent, or Firm* — Wood Herron & Evans LLP

(57) ABSTRACT

Provided is a system for estimating a compliance metric indicating the usage of hygiene equipment by one or more operators, such as in a healthcare setting. The system includes a receiving section and a calculation section. The receiving section is configured to receive activity data from a sensor arrangement, the activity data indicating activities by the one or more operators including usage of the hygiene equipment. The calculation section is configured to estimate, based on the activity data and a trained function, the compliance metric.

7 Claims, 4 Drawing Sheets

(51) Int. Cl.
    *G06N 20/00*         (2019.01)
    *G16H 40/20*         (2018.01)
    *G16H 20/00*         (2018.01)
    *G16H 40/67*         (2018.01)
    *G16H 30/20*         (2018.01)

(52) U.S. Cl.
    CPC ............ *G16H 30/20* (2018.01); *G16H 40/20* (2018.01); *G16H 40/63* (2018.01); *G16H 40/67* (2018.01)

(58) Field of Classification Search
    USPC ........................................................ 705/2–3
    See application file for complete search history.

(56) References Cited

U.S. PATENT DOCUMENTS

2013/0342349 A1    12/2013   Cruz
2016/0005328 A1*   1/2016   O'Toole ............. G09B 19/0076
                                              434/262

OTHER PUBLICATIONS

European Patent Office, Communication Pursuant to Article 94(3) EPC issued in application No. 16 726 536.2-1213, dated Mar. 2, 2021, 7 pages.

Hastie, T., et al., "The Elements of Statistical Learning. 2nd ed.," 2001, Springer, entirety thereof (Abstract provided for updated 2009 book, ISBN information on Abstract, 1 page).

World Health Orginization, "Five Moments of Hand Hygiene," WHO, 2016 (Updated to "Five moments for hand hygiene" WHO, 2021 at https://www.who.int/gpsc/tools/Five_moments/en/) 2 pages.

\* cited by examiner

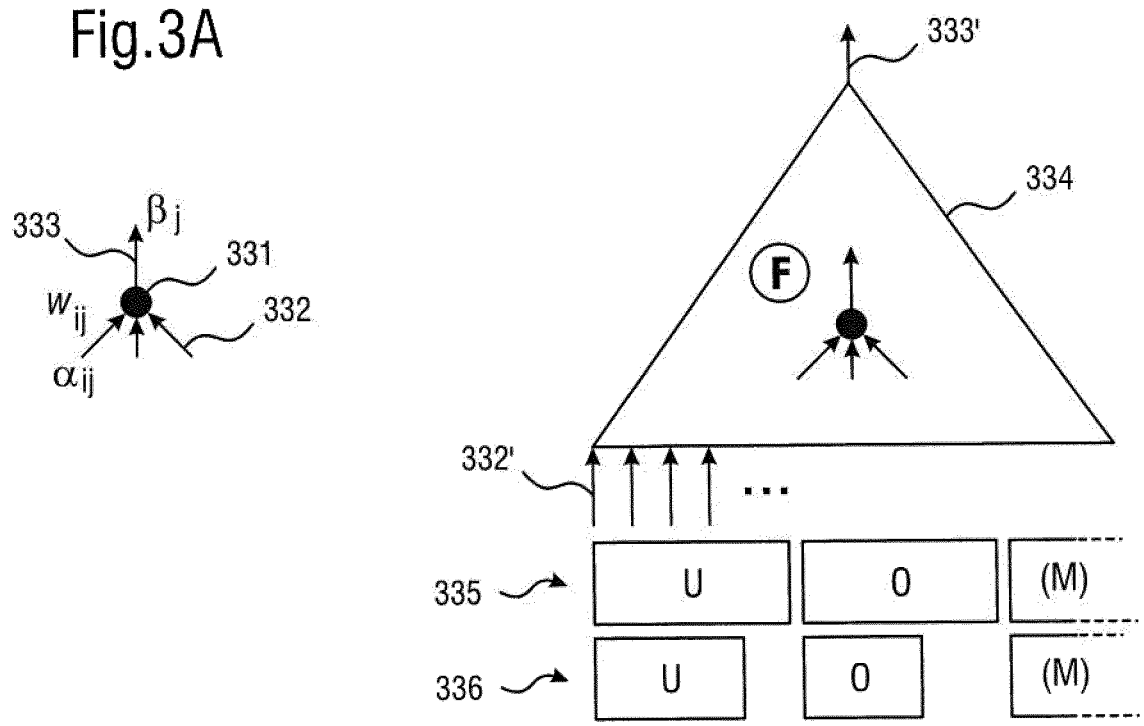
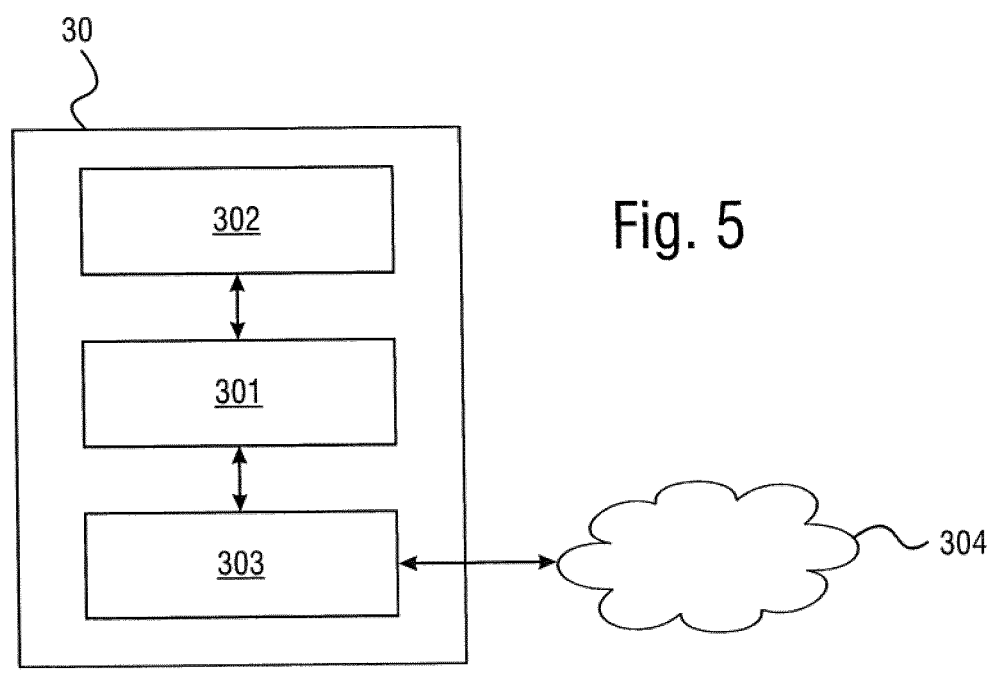

COMPLIANCE METRIC FOR THE USAGE OF HYGIENE EQUIPMENT

CROSS-REFERENCE TO PRIOR APPLICATION

This application is a § 371 National Stage Application of PCT International Application No. PCT/EP2016/062154 filed May 30, 2016, which is incorporated herein in its entirety.

TECHNICAL FIELD

The present disclosure generally relates to estimating a compliance metric in the context of hygiene equipment, such as soap, disinfectant, and/or towel dispensers, and the like. More particularly, the present disclosure relates to ways of determining a value of compliance metric estimate that indicates the actual usage of hygiene equipment by corresponding sensors.

BACKGROUND

Hygiene equipment is commonplace today in many facilities, such as hospitals, medical service centers, intensive care units, day clinics, private practices, lavatories, rest rooms, hotels, restaurants, cafes, food service places, schools, kindergartens, manufacturing sites, administration and office buildings, and, in general, places and facilities that are accessible to the public or to a considerable number of individuals. The mentioned hygiene equipment thereby includes various types of individual devices and installations such as soap dispensers, dispensers for disinfectant solutions, gels or substances, towel dispensers, glove dispensers, tissue dispensers, hand dryers, sinks, radiation assisted disinfectant points, and the like.

Although such hygiene equipment is commonplace today in many places, the use thereof by the individuals visiting these places or working in these places is still oftentimes not satisfactory. For example, hospitals, and, in general, medical service centers often suffer from hygiene deficiencies, which, in turn, may lead to the spread of infections and related diseases. In particular, such insufficient hygiene amongst medical care personnel coming into close contact with patients and bodily fluids can lead to the spread of infectious diseases amongst the personnel and other patients. It is also known that infections by highly resistant bacteria pose a severe problem in such places, above all, hospitals. In general, so-called Healthcare Associated Infections (HAI) are a real and tangible global problem in today's healthcare. HAI can be found to be currently the primary cause of death for 140.000 patients/year, affecting millions more and costs society more.

At the same time, however, it is known that hygiene, and, in particular, hand hygiene, is an important factor as far as the spread of infectious diseases are concerned. Specifically, medical care personnel should make proper use of hand hygiene as often as possible so that the spread of bacteria and other disease causing substances is minimized. The actual usage of such hygiene equipment, however, may depend on—amongst others—the management of the facility, accessibility and usability of the equipment, culture, the cooperation and will exercised by the individuals working in these places or visiting such places, and possibly also other factors. In other words, an important factor remains the fact that individuals may not make use of installed and provided hygiene equipment although they are supposed to. Furthermore, it is generally accepted that an increased use of hygiene equipment can substantially contribute in reducing the spread of bacteria and the like, which, in turn, can drastically reduce the appearance of related infections and diseases.

As a consequence, one may have considerable interest in a so-called compliance that in some way or another compares the actual use of hygiene equipment to some sort of target usage. For example, a corresponding relatively low compliance metric may indicate that the actual use of hygiene equipment is not satisfactory, whilst relatively high compliance metric may indicate that the actual use of hygiene equipment corresponds, within a given threshold, to some target usage, and, consequently, may be regarded as being satisfactory. Such a compliance metric may provide many advantages, since it gives a concise picture to operators of the corresponding facility so that they may initiate measures for increasing the actual use of hygiene equipment. Therefore, there are already ways of estimating such a compliance metric in the arts, wherein the conventional approaches usually rely on measuring and/or observe "manually" by a human observer so-called opportunities and comparing these obtained opportunities to a measured/detected actual use of the hygiene equipment. In other words, the opportunities indicate any event when hygiene equipment should or could have been used. By then comparing this "should/could"-value to an actual usage value a compliance metric can be calculated. In general, the opportunities can be well defined figures, since they may be associated to specific rules and/or recommendations. For example, the World Health Organization (WHO) has defined the so-called "Five Moments Of Hand Hygiene" (cf. www.who.int/psc/tools/Five_moments/en/) including as explicit definitions for opportunities: 1. Before patient contact; 2. Before aseptic task; 3. After body fluid exposure risk; 4. After patient contact; and 5. After contact with patient surroundings.

Moreover, measurements on a corresponding hand hygiene compliance is becoming a regulatory requirement for the healthcare sector and may serve as an important quality improvement tool.

In this context it should be noted that, whilst it is commonplace to implement sensor arrangements in hygiene equipment for measuring the actual usage, it may be more difficult to implement sensor arrangements for measuring, detecting, and/or sensing opportunities. The prior arts generally attempt to improve the sensor arrangement used for sensing/measuring the opportunities for, in turn, improving the accuracy of the obtained compliance metric. However, the optimization of such sensor arrangement for sensing/measuring opportunities in the context of hygiene equipment usage remains complex and difficult, since it may require additional and possibly expensive hardware, equipment, or resources. Moreover, surveillance equipment may also interfere with privacy regulations when corresponding opportunity sensor equipment includes cameras, position tracking systems, or related image and data-processing systems. Thus, even though systems for hand hygiene compliance monitoring may exist, no global standard has been established. The global golden standard for hand hygiene compliance measurement is still to employ a manual observer that observes the hand hygiene practices for a certain time period and calculates the hand hygiene compliance rate based on this observational period. Naturally, manual observation is open to criticism due to its limited time and scope and the bias it will introduce in the measurements.

There is therefore a need for an improved system and method of estimating a compliance metric that improves accuracy of the measured compliance, whilst being as little as possible dependent on complex, expensive, and/or undesired equipment or otherwise labor-intense surveillance and measurement techniques.

SUMMARY

According to one aspect, there is provided a system for estimating a compliance metric indicating the usage of hygiene equipment by one or more operators, the system including a receiving section configured to receive activity data from a sensor arrangement, said activity data indicating activities by the one or more operators including usage of said hygiene equipment, and a calculation section configured to estimate, based on said activity data and a trained function, said compliance metric.

According to another aspect, there is provided a method for estimating a compliance metric indicating the usage of hygiene equipment by one or more operators, the method including a step of receiving activity data from a sensor arrangement, said activity data indicating activities by the one or more operators including usage of said hygiene equipment, and a step of estimating, based on said activity data and a trained function, said compliance metric.

BRIEF DESCRIPTION OF THE DRAWINGS

Embodiments of the present invention, which are presented for better understanding the inventive concepts but which are not to be seen as limiting the invention, will now be described with reference to the figures in which:

FIGS. 3A and 3B show schematic views in conjunction with a neural network being used as a function;

FIG. 5 shows a schematic view of a general entity.

DETAILED DESCRIPTION OF PARTICULAR EMBODIMENTS

Figure 1:
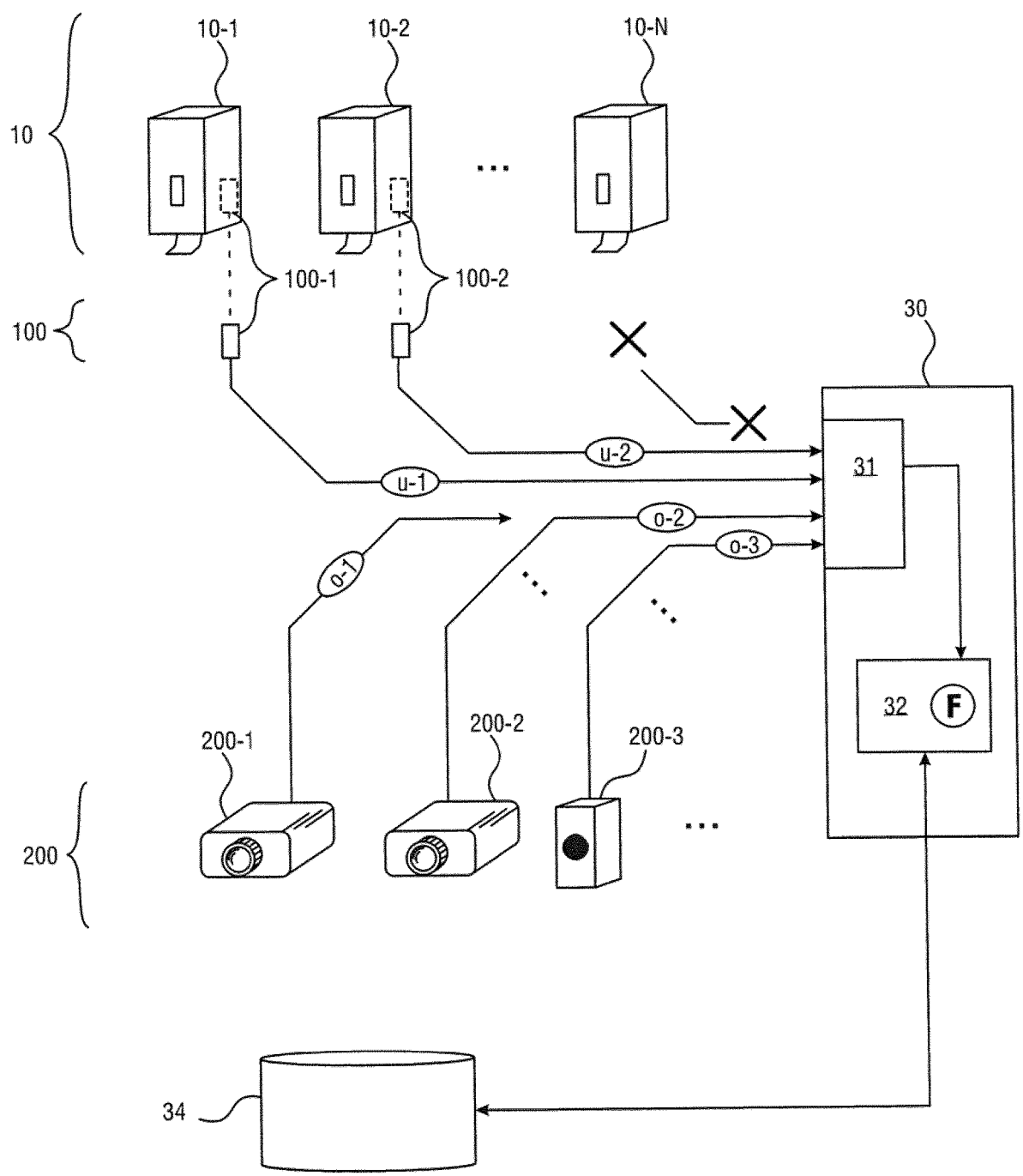
FIG. 1 shows a schematic view of a deployment of a system for estimating a compliance metric.

FIG. 1 shows a schematic view of an embodiment of a deployment of a system for estimating a compliance metric. The system is generally deployed for estimating a compliance metric that indicates the usage of hygiene equipment 10, in the form of, for example, a number of individual pieces of hygiene equipment such as the shown soap or disinfectant dispensers 10-1, 10-2, and 10-N. Generally, the hygiene equipment 10 can include any one of a soap dispenser, a dispenser for disinfectant solutions, gels or substances, a towel dispenser, a glove dispenser, a tissue dispenser, a hand dryer, a sink, a tap, and a radiation assisted disinfectant point, and the like. Such equipment is generally deployed in a facility being any of a hospital, a medical service center, an intensive care unit, a day clinic, a private practice, a lavatory, a rest room, a restaurant, a café, a food service place, a school, a kindergarten, a hotel, a manufacturing site, an administration or office building, a shopping center, and, in general, any places and facility that is accessible to the public or to a considerable number of individuals.

The system 30 includes a receiving section 31 that is configured to receive activity data from a sensor arrangement that generates signals which indicate activities by the one or more operators that are to use the hygiene equipment. In the shown embodiment, the sensor arrangement can be grouped into a so-called use sensor arrangement 100 and a so-called opportunity sensor arrangement 200. The use sensor arrangement can be implemented in the form of an equipment sensor arrangement 100 that forms part of the hygiene equipment 10. Such equipment sensor arrangement 100 is a collection of all available sensors that are able to generate and forward individual usage signals u-1, u-2, . . . that indicate an actual use of some or a specific piece of hygiene equipment. For example, a soap dispenser 10-1 may be provided with a sensor 100-1 that is configured to generate a usage signal u-1 whenever an operator actually uses the piece of hygiene equipment and ejects an amount of soap. In this way, the receiving section 31 receives part of the activity data in the form of individual signals u-1, u-2, . . . and may thus store this data in a database 34. In a way, the actual use of the hygiene equipment by the one or more operators is identified as one kind of activity by the one or more operators within the scope of what is detectable as activity data by the sensor arrangement.

The signals u-1, u-2, . . . are typically signaling "now it happened" (e.g. by carrying a Boolean value "TRUE" or by simply carrying data such as a dispenser ID). In a way, the mere fact that a signal is received may indicate to the system 30 that a usage event happened. However, the signal may also include more information, including information on when the piece of hygiene equipment was used (e.g. timestamp), information on how much of the dispensed substance was used (e.g. dosage size, number of towels etc.), information on who was using it (if the individual operator is tagged and sensed by the system), and/or information on what was used if it is a multi-dispenser containing, for example, both soap and paper. Generally, the collected data may be "imperfect" and may not be complete in the sense that not every actual usage event may be captured, since not every piece of hygiene equipment may be provided with a corresponding sensor. However, the present embodiment assumes that the captured fraction of usage data is good enough to sufficiently represent the usage of the hygiene equipment.

The receiving section 31 of the system 30 may further be configured to receive a further part of the activity data in the form of so-called opportunity data from a corresponding opportunity sensor arrangement 200. The opportunity data indicates a set of opportunities to use the hygiene equipment 10 and this opportunity data is collected by means of receiving individual data signals o-1, o-2, o-3, . . . from corresponding individual pieces of the sensor arrangement 200 such as cameras 200-1, 200-2, vicinity and/or door passing sensors 200-3, and the like. Generally, the opportunity sensor arrangement 200 may be any selection of cameras, low resolution cameras (so it may be difficult to identify individuals in the image data), time-of-flight cameras, infrared (IR) cameras, heat/thermo-cameras, microphones, image recognition resources, vicinity sensors, radar, ultrasonic sensors, IR sensors, photocell sensor, conductive and/or capacitive sensors (presence, touching), laser range sensors, time-of-flight sensors (e.g. sensors that employ the delay of RF-, e/m-pulse or light signals for determining a location, a distance and/or movements), MD readers and/or NFC equipment (e.g. also for identifying a badge carried by an operator), door pass sensors, a light barrier, and the like.

The collected opportunity data signals o-1, . . . are then stored by the system 30 again in the database 34.

Similar to the signals u-1, u-2, . . . the signals o-1, o-2, o-3, are typically signaling "now there is/was an opportunity" (e.g. by carrying a Boolean value "TRUE" or by simply carrying data such as a dispenser or location ID). In a way, the mere fact that a signal is received may indicate to the system 30 that there is an opportunity to use some piece of hygiene equipment. However, the signal may also include more information, including information on when the piece of hygiene equipment could have been used (e.g. timestamp), information on how much of the dispensed substance should have been used (e.g. dosage size, number of towels etc.), information on who could have used it (if the individual operator is tagged and sensed by the system), and/or information on what could have been used by the operator if there are alternatives (for example, soap, towel, or disinfectant). Alternatively or additionally, the opportunity data or signals may also include information on a physical movement of a person or object throughout the facility. In this way also indirect indications to opportunities to use the hygiene equipment may be considered.

The system 30 further includes a calculation section 32 that is configured to employ a trained function F for estimating the compliance metric from the received activity data including, for example, the usage data U and the opportunity data O, retrieved from the database 34 or received ad hoc from the receiving section 31. Generally, the calculation section 32 employs the trained function F which is a set of correlation parameters that allows for estimating a compliance metric from a given set of activity data. In embodiments, the function F is trained in the sense that it can correlate specific activity data patterns to a compliance metric in a fashion as accurate as possible. In an embodiment, the function F is implemented as a machine/statistical learning structure as explained in greater detail elsewhere in the present disclosure.

Generally, the training can be accomplished by human observers and/or more sophisticated sensor arrangements (e.g. including more cameras, image processing, image evaluation, and the like), wherein such costly and complex arrangements can be advantageously dispensed with later during actual operation of the system. For this purpose, "true" compliance metrics can be collected by temporarily deploying a more advanced system and/or one or more human observers who enter the data into an input device (keyboard, smartphone, tablet computer, etc.) that, in turn, generates and forwards a corresponding signal for training the function. In this way, the system can be trained to reproduce (estimate) a compliance metric from activity data that the system knows to correspond to a specific compliance metric.

Figure 4A:
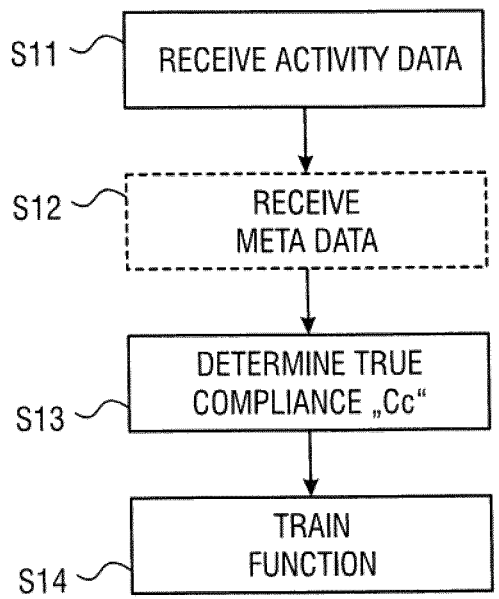
FIG. 4A shows a flowchart of an example of a way to determine parameters of a function.

A general example is shown in conjunction with the flow chart of FIG. 4A that is to show an example of a way to determine parameters of a function in the sense of training the function or to establish the function in a training phase. In a step S11, activity data is received either sequentially or concurrently with determining a true compliance Cc in step S13 as described above (note that the depicted order may likewise be reversed for sequential reception so that the opportunity data is received prior to receiving the usage data). Optionally, and either sequentially or concurrently relative to any one of steps S11 and S13, there can be received metadata in a step S12 (note that the depicted order may likewise be reversed for sequential reception so that the receiving the usage data, determining Cc, and, optionally, receiving the meta data may take place in any suitable order). Since the received activity data provides an actual picture for both the use as well as the opportunities, and since the true compliance metric is known from step S13, the function F can be trained in step S14 so as to map the activity data A to the compliance metric Cc in the way of:

$$Cc=F(A);$$

For example, the collected activity data for an observation period during training may be assessed during step S13 to correspond to, for example, 1000 opportunities, whilst the data indicates for a corresponding period 920 usage events, so that the complete compliance metric Cc in step S13 could be calculated to Cc=920/1000=0.92. The function F is thus trained so as to produce this value for the compliance metric when fed by the respective A. The function F can be further established as F (U, O)=Cc where an explicit differentiation is made into usage U and opportunities O. In addition to this, the calculation section 32 can also process metadata M for evaluating the function F as is, however, explained in greater detail in conjunction with the corresponding embodiments.

Accordingly, there can be provided the advantage that the system only needs to be "trained" for a limited amount of time with relatively complex opportunity sensor arrangements and/or human intervention, whilst it can be then operated with only relatively limited or little effort. The embodiments with regard to a "learning phase" and an "operation phase" are explained in greater detail in conjunction with FIGS. 4A, 4B, and 4C.

In any way, however, the calculation section 32 can be configured, for example, to employ the function F as a product of a machine learning procedure. In such procedures, some initial parameters are preset or randomly chosen and the resulting output (here for example the output compliance metric estimate) is compared to a target value that the function F should reproduce for a given set of input data. This is fed back to the procedure that iteratively adjusts the employed parameters so as to match the target output. In a way, during such a machine learning procedure the calculation section 32 can be "trained" so as to determine the suitable parameters.

Machine learning can be generally identified as a set of algorithms and procedures enabling a computing apparatus (computer) to make analysis and predictions based on incomplete data. Many of these algorithms, such as Artificial Neural Networks, are indeed inspired and try to mimic the function of our nerves and brain. A synonym used often alongside machine learning is the so-called "statistical learning" which is a collection of relevant base techniques that are—as such—known and documented e.g. in T. Hastie et al.: "*The Elements of Statistical Learning*" ($2^{nd}$ edition, Springer, ISBN: 978-0-387-84857-0).

As an example, the calculation section 32 can be thus configured to employ the function F as a set of correlation parameters from activity data acquired for the actual use of the hygiene equipment 10 by the sensor arrangement 100 and the additional opportunities measured/detected by the opportunity sensor arrangement 200 at the same time or during at least in part overlapping intervals. In this way, the opportunity sensor arrangement 200 may at least to some extent provide a sufficient measurement of the opportunities in order to estimate a compliance metric. At least parts of the usage data and the opportunity data are correlated by these parameters to the observed "true" compliance, so that also during further operation without any observer, the acquired data can still be correlated to the compliance by using the parameters of the function.

Figure 2:
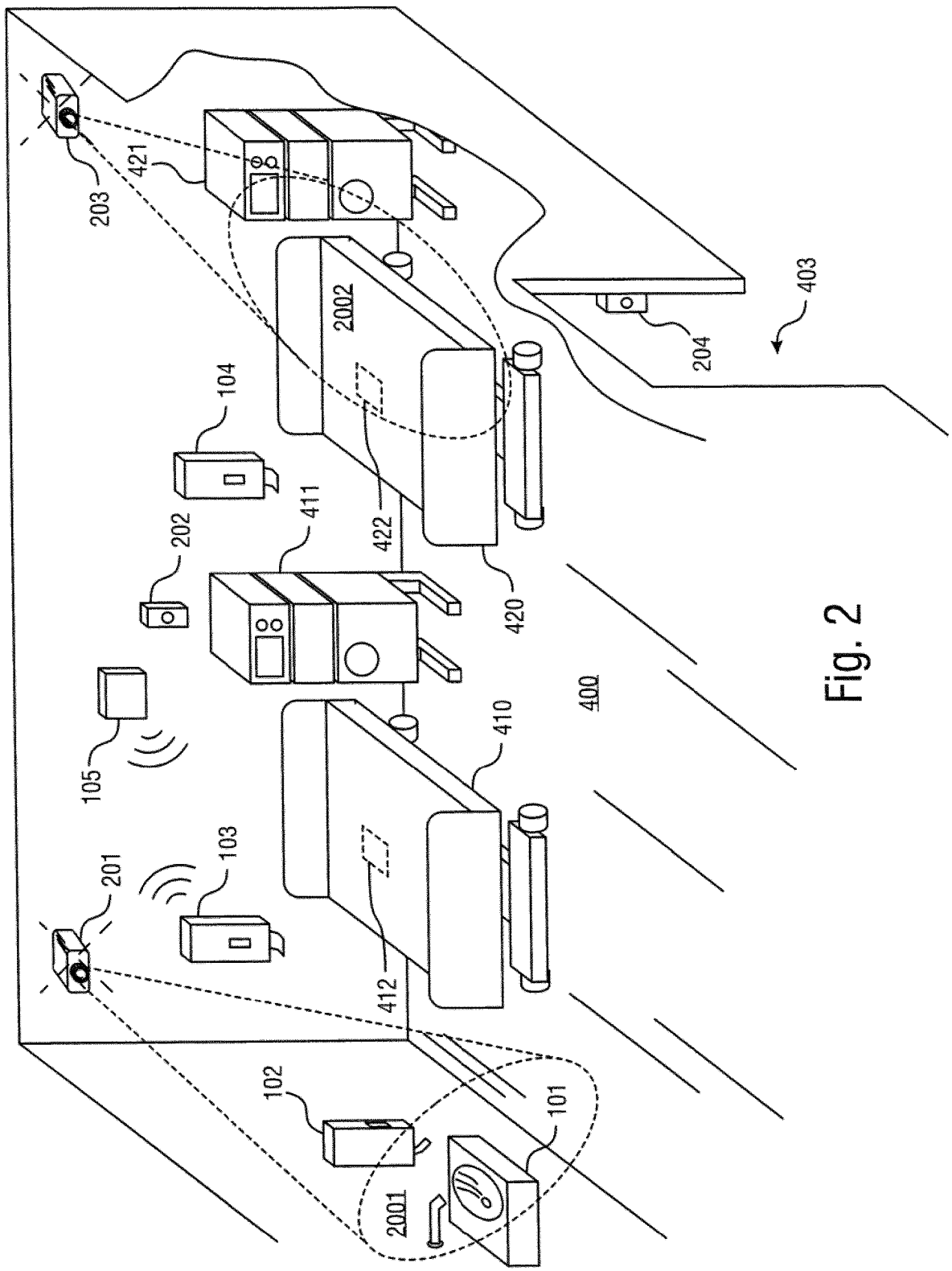
FIG. 2 shows a schematic view of a deployment of a system for estimating a compliance metric.

FIG. 2 shows a schematic view of an example of a deployment of a system for estimating a compliance metric. As an example, there is shown as a facility an intensive care unit 400 with corresponding intensive care points: first and second patient stations 410,420 and first and second patient care equipment 411,421. As can be seen, the intensive care unit 400 may be occupied by one or two patients in the shown configuration, whilst embodiments of the present disclosure may naturally envisage also other intensive care units with any number of patients and personnel and/or other facilities as mentioned elsewhere in the present disclosure.

In general, however, the number of actually occupied intensive care points (beds) as well as other information (e.g. on a number of individuals working/visiting, on a shift, a time of day, a day of week, a holiday) can be considered as optional metadata M, likewise stored, for example, in the database of FIG. 1. Further examples include information on a type of care given (intensive, orthopedic, surgery, child, emergency, ear/nose/throat, etc.) and data measured by corresponding equipment (e.g. a pressure/weight sensor in a bed to indicate if there is a patient in the bed or not). Said metadata M can thus contribute in the calculation section 32 when determining the function F and/or contribute when estimating the compliance metric based on the function F and the activity data. For example, the metadata M can contribute in rendering the function F sensitive to the actual environment (e.g. beds occupied or not) so that it can produce an improved estimate Ce for situations when all or most beds are occupied and when only some beds are occupied.

In an embodiment, the metadata M contributes to the accuracy of the function F in a way that specific scenarios of metadata and opportunity data and/or user data correspond to respective scenarios. For example, the metadata is obtained through receiving signals from pressure (or heat) sensors 412, 422. If one or more of such sensor signals indicate that a corresponding patient station 410, 420 is in use, the opportunities for the use of hygiene equipment will accordingly change. For example, an algorithm may correlate signals from the vicinity sensor 202 and the sensors 412, 422, in a way that signals that indicate an activation of the vicinity sensor 202 (i.e. operator present) and a first pressure sensor 412 correlate to opportunities only in connection with the first patient station 410, whilst signals that indicate an activation of the vicinity sensor 202 and the first pressure sensor 412 and the second pressure sensor 422 correlate to opportunities in connection with both patient stations 410, 420. Accordingly, the parameters of the function F may be compiled in the way that the metadata influences the scenarios and influences the output compliance metric from the activity data.

The configuration shown in FIG. 2 may be representative for both a first learning phase during which the system's function is trained as well as for the actual later operation phase. Specifically, activity data can be acquired from an equipment sensor arrangement provided for one or more of the individual pieces of hygiene equipment, such as the soap dispenser 102, the first and second disinfectant dispensers 103, 104, and the hand washing sink 101. In this way, the system is able to receive usage data U from these pieces of equipment 101-104 as possible individual signals from each corresponding device/sensor. During this phase, also some opportunity sensor arrangement is provided in the intensive care unit 400 that includes one or more cameras 201, 203, a vicinity sensor 202, and a door passing sensor 204. Thereby, the first camera 201 may be in particular arranged for detecting an opportunity in a dedicated area, such as the surrounding area 2001 of the hand wash sink 101. For example, the image and/or video data obtained from first camera 201 may be processed or analyzed for determining whether an individual could have used the soap dispenser 102 when washing his/her hands at sink 101. In a way, the use of the sink 101 implies also an opportunity to use the soap dispenser 102. However, the configuration as shown in FIG. 2 is only to be seen as an application example and other embodiments may well be applicable also to configurations different from the environment of an intensive care unit in particular, or from a hospital in general.

Similarly, second camera 203 may observe a further dedicated area 2002 that covers the vicinity and area of second patient station 420, which can be, for example, a bed. In an example, the corresponding image and/or video data from the second camera 203 may be processed or analyzed in order to find an individual entering the area of the second patient station 420 and/or determining the duration and time for how long the individual remains in the vicinity thereof. This could likewise imply an opportunity to use the first disinfectant solution dispenser 104 before or at the early stage of entering the area 2002 that covers the vicinity and area of the second patient station 420. Such visual determination of an opportunity by images and/or a human observer may also be selected for opportunities that are difficult to detect by sensors, such as a healthcare worker performing an aseptic task (WHO moment Nr. 2) or after a body fluid exposure risk (WHO moment Nr. 3). It may be preferable to further consider that WHO moments Nr.s 1 & 5 may be correlated to moments 2 & 3, which can be exploited for removing sensors that either sense moments 1 & 5 or 2 & 3 in the second opportunity sensor arrangement.

Likewise, a vicinity sensor 202 may determine the opportunity to use the second disinfectant dispenser 104 when an individual operates first patient care equipment 411 which, in turn, can indicate that manual operations or actions are carried out to patient in first patient station 410, which can be, for example, a bed. In general, any one of the equipment sensors and opportunity sensors may convex signals in any suitable manner, such as by wire-bound communication or wireless communication as, for example, shown between the first disinfectant dispenser 103 and a wireless data acquisition and collection point 105.

As already mentioned, however, the use of first and second cameras 201, 203, or in general a complex opportunity sensor arrangement, may be problematic for various reasons. For example, the analysis and processing of the corresponding and produced image or video data may be expensive, since, for example, sufficiently powerful image processing hardware needs to be employed or a human operator may need to view the image data so as to "manually" determine the corresponding opportunity data. Furthermore, the use of such cameras may require the consent of individuals and personnel being present or active in the intensive care unit 400. At the same time, however, it may be tolerable that cameras are installed for a limited time so that the more expensive opportunity sensor arrangement can be deployed for an initial learning phase, when the function of the system is trained. Generally, the training may involve associating the activity patterns detected by the respective sensors to a "true" or assumed compliance metric as, for example, determined by one or more human observers or equipment during the learning phase.

At a later (operation) stage, the deployed opportunity sensor arrangement may be reduced in the sense that some individual pieces of opportunity sensor equipment is removed and/or deactivated. For example, at a second phase, the first and second cameras 201 and 203 may be unmounted so that a specific consent to individuals and or personnel in the context of video surveillance may no longer be necessary. Likewise, any expensive or burdensome analysis of the corresponding image or video data may no longer be necessary. At the same time, however, a somewhat reduced second opportunity sensor arrangement remains active within the intensive care unit 400 as, for example, consisting only of the vicinity sensor 202 and the door passing sensor 204. Furthermore, metadata sensors may be still employed, such as a pressure/weight sensor for determining whether a bed is occupied or not.

In an embodiment a compliance metric is estimated from the activity data in the form of usage data that may well be still available to a high degree of completeness and a somewhat reduced opportunity data received only from the vicinity sensor 202 and door passing sensor 204 from the function F that was previously determined and trained based on the activity data and the associated observed "true" compliance metric.

FIGS. 3A and 3B show schematic views in conjunction with a neural network being used for determining (training) and for later using this function. In a way, the employment of a neural network is one way of using a function as a product of a machine learning procedure. Specifically, FIG. 3A schematically shows a node (neuron) 331 of a neural network. As is known, the neuron 331 has one or more inputs 332 and one output 333. In general, the neuron 331 receives input values $\alpha_{ij}$ at the corresponding input 332, multiplies each input value $\alpha_{ij}$ by a corresponding coefficient $w_{ij}$ and form's the corresponding sum $\beta_j = \Sigma_i w_{ij} \times \alpha_{ij}$ at the output 333. Furthermore, the output $\beta_j$ could also be normalized to a value between 0 and 1, or be made binary so that it either assumes 0 or 1 ($\beta_j \in \{0, 1\}$) by means of applying a rounding and/or Heavyside function. As then shown in FIG. 3B, a neural network 334 is composed of a corresponding manifold of neurons 331 as one is individually shown in FIG. 3A. As a consequence, the network 334 provides at the bottom a number (e.g. k) of inputs 332' receiving the $\alpha_{k1}$ (at k inputs) and, after one or more hierarchy levels of individual neurons 331, at the output 333' the output $\beta_l$ of the topmost neuron of the network 334.

In an embodiment, the calculation section of the system employs such a neural network 334 for both determining the function F from initial (learning) activity data 335 including, for example, user data U, opportunity data O, and, optionally, meta data M. In this phase the neural network is trained so that the output at 333' matches a specific compliance metric C as observed (e.g. a true use rate divided by a true opportunity rate). Here, the neural network 334 can be trained with this data to determine the coefficients $w_{ij}$. In other words, the $w_{ij}$ are trained so that the network 334 gives the correct Cc at output 333' for the given activity data (U, O, and, optionally, M). It is noted that in the context of the present embodiment, a group of or the entirety of the determined coefficients $w_{ij}$ corresponds to the function F as mentioned elsewhere in the present disclosure. In other words, the neural network 334 with the trained coefficients $w_{ij}$ represents the function F in this embodiment.

In an embodiment, the trained neural network 334 (function) is employed to determine at the output 333' a value Ce of an estimated compliance metric based on a second set of activity data 336 that is received during operation. It is noted that the usage data U as part of data 335 may be recorded at the same time, or at least at overlapping intervals, during which the opportunity data O and the meta data M of data 335 is obtained. Likewise, the user data of the data set 336 may be determined (measured, detected) while the corresponding opportunity data, and, optionally, the second meta data is obtained. In a certain embodiment, the time periods during which O and U are measured are the same.

In an operation phase, the function F can then be employed to provide the compliance metric Ce from the activity data (e.g. 336) so as to be an accurate estimate to a corresponding "true" or "complete" compliance metric Cc. An implementation would consider feeding the function with the activity data as inputs to the function F in the same way as in the training phase (see above). However, since the function F is now trained and the corresponding parameters have been learned, an algorithmic implementation would need to evaluate the mentioned inputs with the learned parameters. The latter learned parameters provide that the output compliance metric Ce is calculated taking into account the learned correlations and that the output is an accurate mapping of the compliance metric Cc. In other words, FIGS. 3A and 3B depict two process steps in one, namely the training step which calculates the F in an iterative process between the initial set of learning data 335 in relation to a known Cc (at the top of the triangle), and an operational step which uses the known F (in the triangle) which calculates (or estimates) an estimated Ce with the aid of activity data obtained during operation.

Figure 4B:
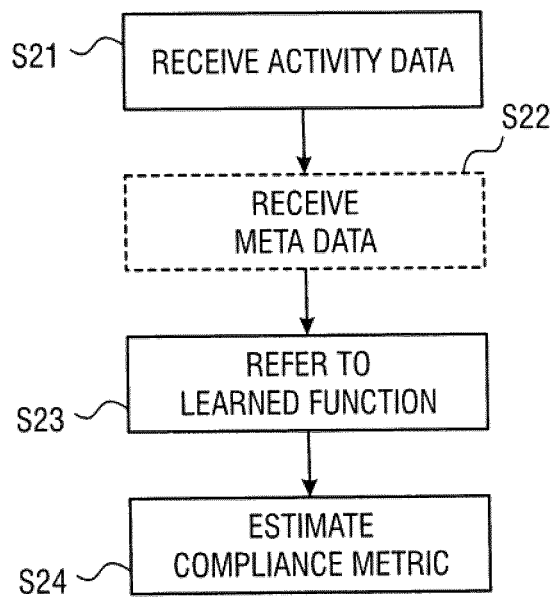
FIG. 4B shows a flowchart of an example of a way to employ the learned function.

With now reference to FIG. 4B, it is described a flowchart of an example of a way to employ the learned function. In step S21, activity data is received either sequentially or concurrently with optionally receiving metadata in step S22 (note that the depicted order may likewise be reversed for sequential reception so that the second opportunity data is received prior to receiving the usage data). It is to be further noted, that the receiving of metadata in the optional step S22 and its corresponding consideration may only make sense when the function was learned with taking into account metadata, as, for example, described in conjunction with FIG. 4A and the optional step S12. Since this embodiment considers that the function F (or its corresponding parameters) is already trained, it can now be referred to this function in step S23, and the compliance metric Ce can be calculated in step S24 by, for example, computationally evaluating the function:

$$Ce = F(A[,M]),$$

Or, in embodiments where an explicit separation into use and opportunity data U and O is made, as $$Ce = F(U, O[,M]),$$

where [, M] means that the consideration of metadata M is optional.

Figure 4C:
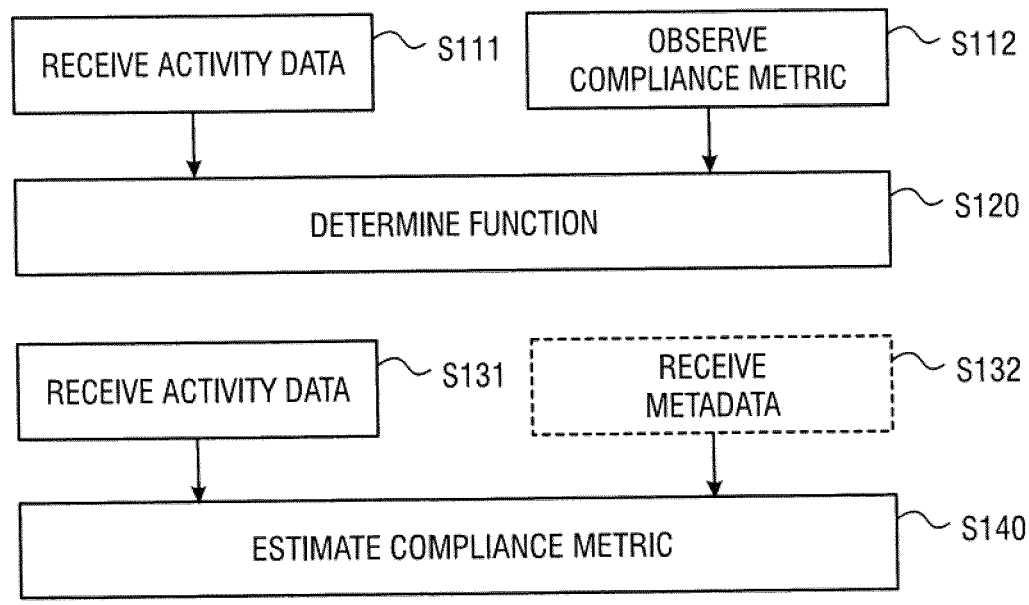
FIG. 4C shows a flowchart of a general method.

FIG. 4C shows a flowchart of a general method. The method embodiments can be implemented for estimating a compliance metric indicating the usage of hygiene equipment by one or more operators. For this purpose, the method embodiments include a first set of steps: a step S111 of receiving activity data (optionally including also meta data) from a corresponding sensor arrangement, a step S112 of obtaining a target compliance metric that a function should reproduce for a given set of input data, and a step S120 of determining, based on said activity data received in the step S111 and the obtained compliance metric a function. This function can then be employed during an "operation phase". Such a phase may be associated with a second set of steps: a step S131 of receiving activity data from the sensor arrangement and an optional step S132 of receiving meta data. In a step S140 it is then estimated the compliance metric from the data received in step S131 and optionally step S132 using said function. Additional phases may be envisaged, where the compliance metric estimated by using the function is verified or confirmed, and/or where the function is optimized and/or fine-tuned for the respective purpose.

In another embodiment, the system is trained with the aim of reaching a stable and robust function F. In an additional test phase it can be determined how reliable the F-function is. This is done by exposing the F-function to another, un-seen, set of "complete" data (O, U) to measure how well the estimated compliance Ce matches the "real" compliance Cc. Then, the operation phase can be initiated as described elsewhere in the present disclosure. In this embodiment the "complete" data can be split in two sub-sets of which one is used in the first training/learning phase and the other in the testing phase.

FIG. 5 shows a schematic view of a general entity. The entity can be any collection of processing and memory resources that are suitable for implementing the corresponding sections of a system for estimating the compliance metric. For example, the entity 30 can be implemented as a stand-alone computer, a server, a processing share of a datacenter, or an application running on some kind of shared hardware. More specifically, the entity 30 schematically illustrated includes processing resources 301 (e.g. CPU), memory resources 302 and communication means 303 (e.g. a receiver/transmitter working according to WLAN, WiFi, WiMAX, Bluetooth™, GPRS, GSM, PCS, DECT, UMTS, 3G/4G/5G, LTE, etc., or a wire-bound standards such as Ethernet and the like) that are configured to communicate with some kind of network 304 (e.g. LAN, wireless communication system, an intranet, the Internet, and the like). By means of the latter, the system is able to receive the usage and opportunity data signals u-i, o-i, etc., access the database 34, or to convey any estimated metric to a given location.

Specifically, the memory resources 302 are adapted to store code that instructs the processing resources 301 during operation to implement at least a receiving section configured to receive activity data from a sensor arrangement, said activity data indicating activities by the one or more operators including usage of said hygiene equipment, and a calculation section configured to estimate, based on said activity data and a trained function, said compliance metric.

Although detailed embodiments have been described, these only serve to provide a better understanding of the invention defined by the independent claims and are not to be seen as limiting.

The invention claimed is:

1. A system for estimating a compliance metric indicating a usage of hygiene equipment by one or more operators, the system comprising:
an equipment sensor arrangement installed in the hygiene equipment, the equipment sensor arrangement configured to generate a signal indicating an actual use of the hygiene equipment by the one or more operators;
an opportunity sensor arrangement arranged in a vicinity of the hygiene equipment, the opportunity sensor arrangement configured to generate a signal indicating an opportunity for use of the hygiene equipment by the one or more operators;
a computing device in communication with the equipment sensor arrangement and the opportunity sensor arrangement, the computing device comprising at least one processor and a memory for storing computer executable instructions that, when executed by the at least one processor, cause the at least one processor to:
receive, from the equipment sensor arrangement, the signal indicating an actual use of the hygiene equipment,
receive, from the opportunity sensor arrangement, the signal indicating an opportunity for use of the hygiene equipment,
receive metadata associated with an environment in which the hygiene equipment is to be used by the one or more operators, the metadata indicating a number of occupied care points;
define a trained function including a plurality of neurons each having one or more inputs and an output, the plurality of neurons being arranged into a plurality of hierarchical levels including a bottom level having a number of inputs equal to the number of received signals and a top level having a single output, each neuron receiving an input value at each input, multiplying the input value by a corresponding coefficient, and outputting a sum of the resulting products, the coefficients being determined by training the trained function to output a compliance metric for a given set of use data, opportunity data, and metadata; and
estimate, using the trained function, the compliance metric based on (i) the signal indicating an actual use of the hygiene equipment, (ii) the signal indicating an opportunity for use of the hygiene equipment, and (iii) the received metadata.

2. The system according to claim 1, wherein the signal indicating an opportunity for use of the hygiene equipment includes data indicating a presence of the one or more operators in the vicinity of the hygiene equipment.

3. The system according to claim 2, wherein the opportunity sensor arrangement comprises a camera, image recognition resources, a vicinity sensor, a door pass sensor, a light barrier, a time-of-flight sensor, RFID readers, or NFC equipment, or combinations thereof.

4. The system according to claim 1, wherein the signal indicating an actual use of the hygiene equipment and the signal indicating an opportunity for use of the hygiene equipment are generated during a same period of time.

5. The system according to claim 1, wherein the hygiene equipment comprises a soap dispenser, a dispenser for disinfectant solutions, gels or substances, a towel dispenser, a glove dispenser, a tissue dispenser, a hand dryer, a sink, a tap, or a radiation assisted disinfectant point.

6. The system according to claim 1, wherein the system further comprises a database configured to store data corresponding to the respective signals received from the equipment sensor arrangement and the opportunity sensor arrangement.

7. A method for estimating a compliance metric indicating a usage of hygiene equipment by one or more operators, the method comprising:
receiving, at a computing device, from an equipment sensor arrangement installed in the hygiene equipment, a signal indicating an actual use of the hygiene equipment by the one or more operators;
receiving, at the computing device, from an opportunity sensor arrangement installed in a vicinity of the hygiene equipment, a signal indicating an opportunity for use of the hygiene equipment by the one or more operators;
receiving, at the computing device, metadata associated with an environment in which the hygiene equipment is to be used by the one or more operators, the metadata indicating the number of occupied care points;

defining, by the computing device, a trained function including a plurality of neurons each having one or more inputs and an output, the plurality of neurons being arranged into a plurality of hierarchical levels including a bottom level having a number of inputs equal to the number of received signals and a top level having a single output, each neuron receiving an input value at each input, multiplying the input value by a corresponding coefficient, and outputting a sum of the resulting products, the coefficients being determined by training the trained function to output a compliance metric for a given set of use data, opportunity data, and metadata; and estimating, by the computing device, using the trained function, the compliance metric based on (i) the signal indicating an actual use of the hygiene equipment, (ii) the signal indicating an opportunity for use of the hygiene equipment, and (iii) the received metadata.

* * * * *